United States Patent [19]

Voss

[11] 4,361,150
[45] Nov. 30, 1982

[54] EXTRUDED PLASTIC HYGIENIC APPLICATOR

[76] Inventor: Joseph A. Voss, 22 Princeton Dr., Rancho Mirage, Calif. 92270

[21] Appl. No.: 138,117

[22] Filed: Apr. 7, 1980

[51] Int. Cl.³ .............................................. A61F 15/00
[52] U.S. Cl. .................................................... 128/263
[58] Field of Search ............... 128/260, 261, 263, 264, 128/271, 285

[56] References Cited

U.S. PATENT DOCUMENTS

| | | | |
|---|---|---|---|
| 2,754,822 | 7/1956 | Emelock | 128/264 |
| 3,347,234 | 10/1967 | Voss | 128/260 |
| 3,433,225 | 3/1969 | Voss et al. | 128/263 |
| 3,575,169 | 4/1971 | Voss et al. | 128/263 |
| 3,628,533 | 12/1971 | Loyer | 128/263 |
| 3,667,465 | 6/1972 | Voss | 128/271 |
| 3,830,236 | 8/1974 | Hanke | 128/263 |
| 3,895,634 | 7/1975 | Berger et al. | 128/263 |
| 4,198,978 | 4/1980 | Nigro | 128/285 |

FOREIGN PATENT DOCUMENTS 1286634  1/1962  France ............................ 128/271

*Primary Examiner*—C. Fred Rosenbaum
*Attorney, Agent, or Firm*—John E. Reilly

[57] ABSTRACT

A novel and improved applicator has been devised for insertion of hygienic mediums, such as, for example, suppositories or tampons, either rectally or vaginally, respectively. The applicator is characterized by having an outer tube provided with a segmental, tapered end which is so formed and constructed as to avoid sharp edges along the segmental end portions and avoid any possibility of damage or injury to sensitive membranes or body tissue when the applicator is inserted. A removable plunger is insertable into the outer tube for the purpose of advancing the hygienic medium through the tube and is characterized by having a tapered end which is limited in its extent of projection through the tube so as to assure complete discharge of the hygienic medium through the segmental end of the tube without expanding the segmental ends beyond the outer diameter of the tube. Limit stops and locator pins are provided between the applicator tube and plunger to limit the distance of movement of the plunger through the tube, and a gripping ring is so formed on the external surface of the tube as to facilitate handling of the applicator. A method of manufacturing has been devised for high volume production of the applicator tube and plunger under close tolerances and in a minimum number of steps and specifically wherein any special cutting or forming operations following extrusion are avoided.

22 Claims, 11 Drawing Figures

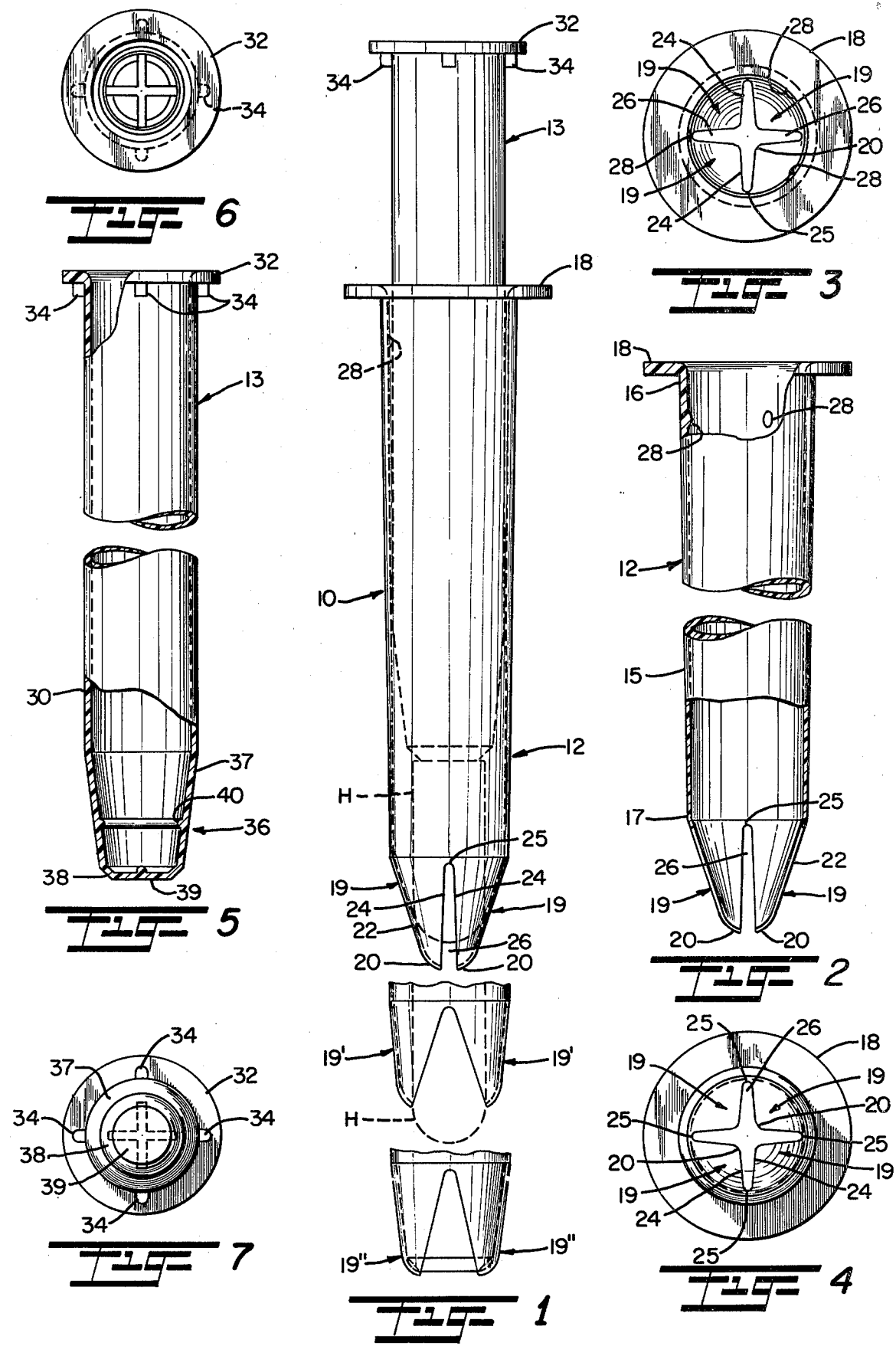

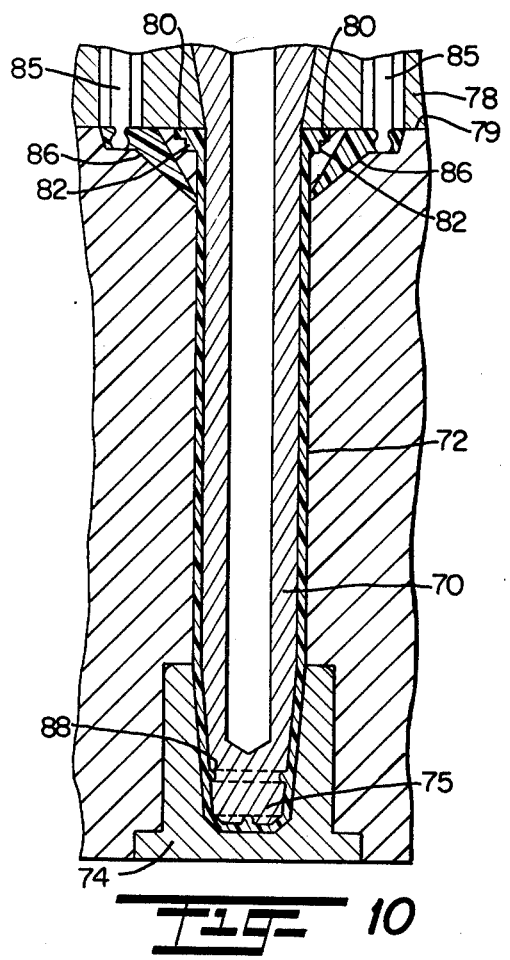
FIG. 10
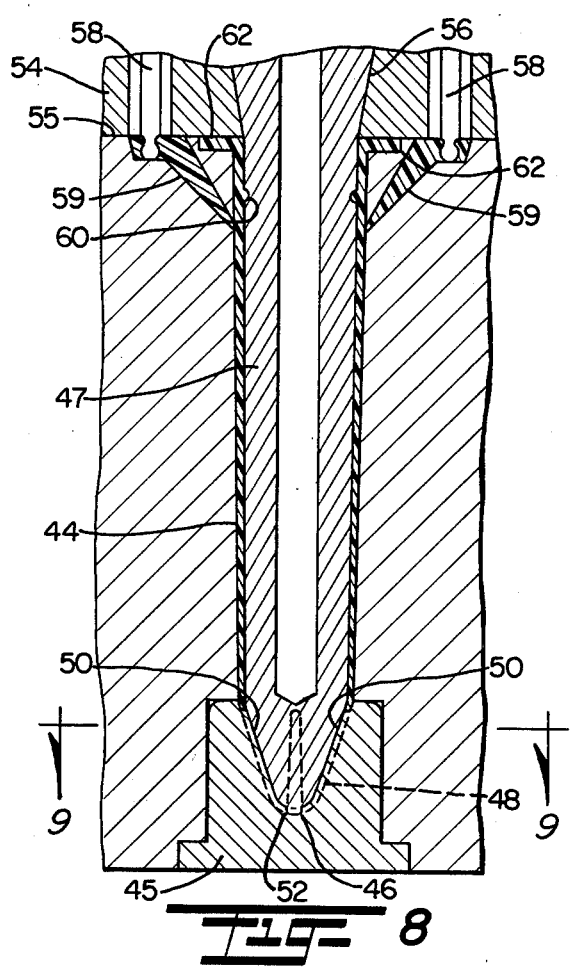
FIG. 8
FIG. 9
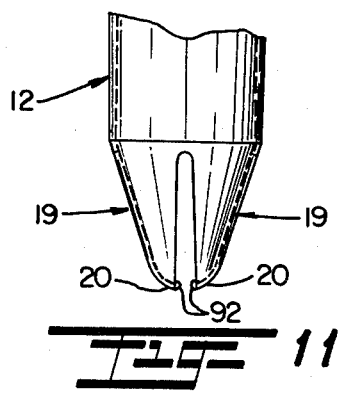
FIG. 11

EXTRUDED PLASTIC HYGIENIC APPLICATOR

This invention generally relates to hygienic appliances and more particularly relates to novel and improved applicators for the retention and selective ejection of suppositories, tampons and the like.

BACKGROUND AND FIELD OF INVENTION

It has been customary in the past to prepackage hygienic media, such as, catamenial or suppository articles within generally tubular applicators which are provided with a plunger so as to facilitate the sanitary ejection of the media into body cavities. Applicators of the type referred to may be best exemplified by references to those disclosed and shown in U.S. Pat. Nos. 3,347,234 to Joseph A. Voss; 3,433,225 to J. A. Voss et al; and 3,575,169 to Joseph A. Voss et al. In each, the applicator is broadly characterized by having an inner tube or plunger element which is telescopingly slidable through an outer tube to advance the hygienic medium through a forward segmental, tapered end. Typically, devices of this type can be fabricated either out of a paper or plastic material but have suffered from the drawbacks of being costly to manufacture, time consuming to assemble and requiring some care in manipulation and use so as to avoid any irritation or discomfort to the user or patient. The use of a segmental, tapered or conical end which will act as a closure across the front end of the applicator for storage of the hygienic medium but is capable of opening for delivery of the hygienic medium under the advancing force of the plunger has been in widespread use and adopted in most all applicators which have been commercialized in recent years. Specifically, the segmental ends have been formed of a series of tightly abutting, dovetailed folds which are capable of unfolding under the opening force of the hygienic medium, as disclosed in the hereinbefore referred to U.S. Pat. No. 3,347,234; or have taken the form of generally triangular segments arranged in abutting relation to one another, for example, as exemplified by U.S. Pat. No. 3,433,225. The last-mentioned patent also suggests the desirability of forming the leading ends of the segments or fingers with transversely rounded extremities and to notch the sides of the segments to form intervening spaces therebetween in order to reduce any frictional resistance which the segments might present to the ejection or discharge of the hygienic medium therefrom. Other more recent patents have alluded to the problem of forming relatively sharp edges along the segmental end of the applicator tube and have proposed to avoid the problem by specialized manufacturing techniques which result in the formation of a rounded contour in cross-section of the leading edges. Typical of this approach are U.S. Pat. Nos. 3,830,236 to Hanke and 3,895,634 to Bergen. However, past attempts to avoid this problem have centered more on the contour of the segmental ends than on the degree of opening of the ends or the complete expulsion of the medium from the outer tube. It has been found in accordance with the present invention that the problem can be most satisfactorily overcome by a combination of regulating the contour of the segmental ends, the plunger and the degree of expansion of the segmental ends under the opening force of the plunger.

SUMMARY OF INVENTION

It is an object of the present invention to provide for a novel and improved hygienic applicator conformable for use with suppositories, tampons and the like to facilitate their safe, rapid insertion into body cavities in an efficient and reliable manner.

It is another object of the present invention to provide for an economical, simplified method of making an applicator assembly for hygienic media which is capable of mass production while holding close tolerances and involving a minimum number of steps.

Another object of the present invention is to provide for a novel and improved hygienic applicator assembly which is characterized in particular by its ability to be readily inserted either rectally or vaginally without any tendency to collapse while avoiding the danger of cutting or pinching body tissues; and further, wherein the applicator assembly is of the type having a male inserter number movable in telescoping relation through an outer applicator tube having a hygienic medium contained therein, the inserter being so designed in relation to the applicator tube as to be capable of substantially complete ejection of the hygienic medium from the forward, segmental end of the applicator tube without expanding the segmental end beyond the normal diameter of the tube.

In accordance with the present invention, a hygienic medium applicator assembly has been devised for the safe, rapid ejection of a hygienic medium into a body cavity. The preferred form of assembly is comprised of an outer, generally tubular member or shell which is adapted to contain the hygienic medium therein. The tubular member includes a forwardly convergent end made up of a series of generally triangular segments which are arranged in circumferentially spaced relation to one another and with adjacent segments being separated by a clearance space of progressively increased width toward the leading end of the tubular member. The segments uniformly converge from the outer wall of the shell progressively along an inclined angle, then follow a sharp curvature into a forward extremity. The side or lateral edges of each segment also converge or taper forwardly and terminate in a common, rounded terminal end at the apex of each segment, the convergent edges of each segment having an included angle of at least 90° therebetween and each of the edges being somewhat rounded or beveled in cross-section. No effort is made to seal or completely close the front end of the applicator tube by means of the segments alone, and the segments are of a length such that they are free to bend readily in a radial direction under the opening pressure of the hygienic medium being advanced therethrough.

A male inserter takes the form of a plunger which is insertable through the opposite, open end of the applicator tube behind the hygienic medium, the plunger having a forward, tapered end which is capable of being advanced through the segmental end of the applicator tube so as to assure the complete ejection of the hygienic medium therefrom without expanding the segmental end portion beyond the outer diameter of the applicator tube. The leading, tapered end of the plunger substantially conforms to the tapered configuration of the inner wall of the segmental end of the applicator tube so that once the hygienic medium is ejected from the segmental end, the segments will be free to contract into closely surrounding relation to the tapered end of the plunger. Preferably, the rearward open end of the applicator tube is provided with a relatively wide but flat gripper ring to facilitate handling and insertion of the applicator assembly into a body cavity, and the rearward end of the plunger is similarly provided with a ring having locator or limit stop elements which abut the gripper ring on the applicator tube so as to limit the extent of penetration or advancement of the plunger through the applicator tube. Further, it is desirable to construct the plunger of a harder material than that of the applicator tube.

Similarly, the method of the present invention is characterized by employing an injection molding process utilizing materials of different hardness to form each of the plunger and applicator shell units in such a way as to closely control the wall thickness of the units and the curvature of the segmental end of the outer shell while eliminating the formation of sharp edges or flashing along the edges which would otherwise require a separate trimming or cutting operation following the molding process. For certain applications, beads may be formed at the leading extremities of the segmental ends so as to form somewhat spherical ends which will completely eliminate the formation of edges or corners at the tips.

The above and other objects, advantages and features of the present invention will become more readily understood and appreciated from a consideration of the following detailed description of a preferred embodiment of the present invention when taken together with the accompanying drawings in which:

BRIEF DESCRIPTION OF THE DRAWINGS

FIG. 1 is a front view in elevation of the preferred embodiment of the present invention;

FIG. 2 is a front view partially in section illustrating the outer applicator tube of the preferred form of the present invention as shown in FIG. 1;

FIG. 3 is an end view of the outer applicator tube taken from the trailing end of the tube;

FIG. 4 is an opposite end view of the applicator tube taken from the leading end as shown in FIG. 2;

FIG. 5 is an elevational view partially in section of the preferred form of plunger as shown in FIG. 1;

FIG. 6 is an end view of the trailing end of the plunger shown in FIG. 5;

FIG. 7 is an end view of the leading end of the plunger shown in FIG. 5;

FIG. 8 is a somewhat fragmentary cross-sectional view of the die components employed in the fabrication of the preferred form of applicator tube;

FIG. 9 is an enlarged cross-sectional view taken about lines 9—9 of FIG. 8;

FIG. 10 is a somewhat fragmentary cross-sectional view of the die components employed in the fabrication of the preferred form of plunger shown in FIGS. 5 to 7; and FIG. 11 is a fragmentary view partially in section of a modified form of applicator tube in accordance with the present invention.

DETAILED DESCRIPTION OF THE PREFERRED EMBODIMENT

Referring in more detail to the drawings, there is illustrated in FIGS. 1 to 7 a preferred form of applicator assembly 10 which is broadly comprised of a first tubular member or applicator tube 12 and a second tubular member in the form of a male inserter or plunger 13 which is insertable in telescoping relation to the applicator tube for the purpose of ejecting a hygienic medium as generally designated at H. For the purpose of describing the preferred form of the present invention and as a setting therefor, the hygienic medium H may be a suppository which is of a consistency such that it is normally solid at room temperatures and will rapidly melt into a gel or liquid-like consistency at body temperature. The suppository is usually bullet-shaped or of elongated generally cylindrical configuration as shown and is adapted to be inserted by placing the leading end of the applicator tube within the rectum and advancing the plunger 13 forwardly through the tube 12 to completely eject the hygienic medium H therefrom.

In accordance with the present invention, the applicator tube 12 is generally in the form of a thin-walled shell having an outer wall 15 which is of progressively reduced diameter from its trailing end 16 to its leading end 17 with a gripper ring 18 positioned at its trailing end and a series of generally triangular segments 19 converging forwardly from the leading end 17 of the wall 15 to terminate in a forward rounded extremity or tip 20. In the preferred form, there are four quadrantal end segments 19 of corresponding size and configuration which converge forwardly in equally spaced circumferential relation to one another from the leading end 17. Each segment 19 inclines forwardly first at an acute angle to the longitudinal axis of the tube along the greater length of the segment as generally designated at 22, then curves more abruptly at its leading end 20 so as to extend substantially transversely to the longitudinal axis of the tube at its extremity.

As viewed in FIG. 4, when taken from the leading end of the applicator tube, each quadrantal end segment 19 has forwardly inclining side edges 24 which are somewhat rounded in contour and converge forwardly from the base 25 to terminate in a common rounded end which forms the leading end or extremity 20. By virtue of there being four quadrantal end segments which are arranged in closely-spaced relation to one another and further by virtue of the length-to-width ratio of the segments, the included angle formed between the inclined side edges 24 of each segment is equal to or greater than 90° so as to result in the formation of a gently sloping rounded extremity or tip 20. In other words, the tip 20 is rounded both in a radial direction inwardly toward the longitudinal axis of the tube and in a circumferential direction in forming a juncture between the inclined edges 24. Preferably, the side edges 24 converge in a direction such that a clearance space or gap 26 formed between side edges 24 of adjacent segments 19 is of a uniform or of a progressively increased width toward the leading end or tip 20. In a manner to be hereinafter described, the segments 19 are composed of a resilient or pliable material and are so formed as to be normally disposed in the substantially closed position as illustrated in FIGS. 1 to 4; and any pressure applied to the tip or leading end 20 will cause the segments to be drawn more closely together. However, once the pressure is removed from the segments, they will tend to spring back into the partially closed position as illustrated in FIGS. 1 to 4. Conversely, if an opening pressure is applied internally of the segments, such as, by the advancement of the plunger 13, to cause the hygienic medium H to be advanced against the inner walls of the segments 19, the segments will readily spread outwardly in a radial direction, as shown in dotted form at 19' in FIG. 1. Again, once the hygienic medium is fully or completely ejected from the leading end of the applicator tube, the segments will return to their normal, partially closed position as illustrated in full at 19".

The gripper ring 18 which is formed at the trailing end of applicator tube 12 is in the form of an integral flange which projects outwardly in a radial direction from the trailing extremity of the tube 12 and takes the form of a thin, extremely wide plate which will facilitate grasping and handling of the tube in a manner to be hereinafter described. Further, a plurality of radially inwardly projecting dimples or lobes 28 are arranged in equally spaced circumferential relation around the inner wall surface of the wall 15 adjacent to its trailing end, the dimples being of generally convex or spherical configuration so as to smoothly guide the suppository or hygienic medium H as well as the plunger 13 for longitudinal advancement through the applicator tube 12.

The preferred plunger 13 takes the form of a generally tubular or hollow cylindrical wall 30 which is of uniform diameter throughout and has an outer diameter corresponding to the inner diameter at the leading end of the wall 15 of the applicator tube. Further, the locator means 28 on the inner wall surface of the tube 12 are dimensioned so as to define an inner effective diameter at the trailing end of the tube 12 corresponding to the outer diameter of the wall 30. The plunger wall 30 is in the form of a thin-walled shell which is provided with a radially outwardly directed, unitary flange 32 at its trailing end provided with a series of uniformly spaced limit pins 34 arranged around the surface of the flange 32 so as to project in a forward direction externally of the wall 30. The plunger 13 includes a forwardly convergent or snub-nosed leading end 36 which is dimensioned to conform to the configuration of the inner wall surfaces of the segments 19 when in the closed position, as best seen from FIG. 1, and to this end is provided with a forwardly convergent sidewall 37 which inclines at an acute angle to the longitudinal axis of the plunger and merges into a more sharply inclined sidewall section 38 which terminates in a squared end surface 39. The sidewall 37 is provided with a rib 40 on its inner wall surface, but most importantly, the sidewall 37 is inclined to correspond to the angle of inclination of the sidewall 22 of each of the segments 19 while the sidewall 38 inclines at an angle more nearly corresponding to the more abrupt curvature of the leading extremities or tips 20 of the segments 19. By virtue of the construction and arrangement of the plunger 13 as described, the plunger is insertable through the trailing end of the tube 12 and is guided in its forward advancement by the locating means 28 to engage or abut the trailing end of the suppository H. Assuming that the suppository is of a diameter corresponding to the leading end of the wall 15, it will, as it is advanced by the plunger, force the segments 19 to spread or expand in an outward radial direction, for example, as represented at 19' in FIG. 1. The plunger as it approaches the leading end of the tube 12 will advance in close-fitting relation along the inner wall surface of the tube so as to insure complete removal and ejection of the suppository through the leading end of the tube until the plunger reaches a point such that its leading end occupies the space within the segmental end of the tube and specifically with the squared end surface 39 disposed opposite to the tips 20. In this relation, the plunger is dimensioned to be of a length corresponding to the length of the tube and is limited in its forward projection through the tube by abutment of the limit stops 34 against the trailing end surface of the gripper ring 18 on the tube. Once the hygienic medium H has been completely expelled from the leading end of the tube, the segments will be free to return to the position as represented at 19" in FIG. 1 in closely surrounding relation to the leading end of the plunger.

A description of the forming operation of the assembly of the present invention will serve to highlight a number of features which are incorporated into the applicator assembly and which make it adaptable for use in applications not practical with the presently available applicators. Preferably, the method is carried out in an injection molding operation where, as illustrated in FIGS. 8 and 9, the outer applicator tube 12 is formed into the desired configuration by an outer generally cylindrical cavity 44 having a counterbored portion at its forward end for insertion of a nose block 45 which is provided with a generally dome-shaped cavity 46 aligned with the wall surface of the cavity 44. A hollow central core 47 is spaced concentrically within the cavity 44 and nose block 45 with a forward conical end 48 of the core being centered within the nose block by equally spaced, inwardly projecting ribs 50 on the inner wall of the nose block 45, as best seen from FIG. 9. The spaced inwardly projecting ribs 50 are arranged at equally spaced circumferential intervals and, in the formation of the series of four segments 19 as described with reference to the preferred form, four ribs are spaced at 90° intervals around the inner wall surface of the nose block cavity 46. These ribs converge into a common central area or space as represented at 52 and which defines the clearance space between the tips 20 of the segments. A rearward support block 54 abuts rearward end surface 55 of the cavity section 44 and surrounds rearward flared end 56 of the central core 47. Injection ports 58 extend through the support block into communication with tunnel gates 59 in outer surrounding relation to the rearward end of the cavity section, the tunnel gates being angularly directed from the injection ports to converge forwardly into communication with the space formed between the central core 47 and outer cavity section 44. Slight indentations 60 are formed at equally spaced circumferential intervals around the external wall surface of the central core 47 adjacent to the rearward end surface 55 of the cavity to form the locators 28; also a radial space 62 is formed between the rearward end of the cavity section 44 in surrounding relation to the core and which is designed to form the radially outwardly projecting gripper ring 32 on the applicator tube 12.

In forming the applicator tube 12, preferably a low density polyethylene material is employed which has the characteristic of curing into a relatively soft, pliable wall section, for example, when formed to be on the order of 0.005" in wall thickness. The pliability or resiliency of the material is most pronounced in the segmental ends 19. The material is injected through the injection ports 58 under pressure so as to flow through the tunnel gates and evenly throughout the space formed between the outer cavity section 44 and central core 47 so as to completely and uniformly fill the spaces as defined. In accordance with well-known practice, gases are vented through openings, not shown, in the nose block 45, which gases tend to form and collect as the molded plastic material is injected in the cavity.

In a similar manner, the inner plunger 13 is formed by an injection molding process in which a central core 70 is positioned within an outer cavity section 72, the latter provided with a forward nose block 74 having a generally frustoconical cavity 75 which aligns with the inner wall of the cavity section 72. The leading end of the core 70 and the cavity 75 within the nose block 74 are formed with correspondingly angled surfaces which result in the formation of the end surfaces 37 and 38; and the leading end of the core as well as the closed end of the cavity area 75 are correspondingly squared to result in the formation of the squared end surface 39. Again, the core is supported in position by a rearward support block 78 which abuts the rearward end surface 79 of the cavity section 70, and a radial space 80 is formed in the cavity wall along the rearward end surface 79 of the cavity wall for the purpose of forming the radially directed end surface 32 at the rearward end of the plunger. Bores 82 are formed at spaced intervals in the cavity wall in communication with the space 80 for the purpose of forming the limit stop elements 34 around the end surface 32.

As in the case of the molding of the applicator tube, injection ports 85 extend through the support block 78 into communication with tunnel gates 86 for the injection of plastic material into the mold. A circular groove 88 is formed at the external surface of the core 70 adjacent to its leading end for the purpose of forming the internal rib 40 on the inner wall of the plunger. Suitable bores, not shown, are provided in the nose block 74 for expulsion of gases which collect in the mold during the formation of the plunger 13. In this relation, most desirably a high density polyethylene material is employed so as to result in the formation of a harder, substantially rigid plunger element, as opposed to the relatively soft pliable applicator tube. Again the material is injected under pressure through the tunnel gates to uniformly fill the space between the core and cavity and to form a plunger having a uniform wall thickness with a uniform diameter throughout its length, except at the leading end or nose of the plunger as previously described. This wall thickness will generally correspond to that of the applicator tube and be on the order of 0.005" thick. While the wall thickness of the applicator tube 12 is uniform throughout its length, preferably, the diameter of the tube will progressively decrease at a low gradual angle, then merge into the segmental end, the segments extending at a relatively low gradual angle from the outer wall of the tube. Preferably the angle of the segments with respect to the longitudinal axis is less than 20° and, which coupled with the cross-sectional curvature of the segments, will assure that the segmental ends do not collapse when the applicator tube is inserted into a body cavity. At the same time, the soft pliable composition of the segments will permit them to readily expand under the opening pressure of the suppository. Once the plunger 13 has entered the segmental end and reached the tips of the segments so as to insure complete ejection of the suppository, the segments 19 will be free to return to their normal, partially closed position as illustrated in FIG. 1. In this position, a slight spacing between the fingers will minimize any tendency of the fingers to pinch the skin or body tissue as the applicator is withdrawn from the cavity. The plunger cooperates in this respect in preventing contraction of the segments into abutting relation.

The slight rounded contour given to the inclined side edges 24 of the segments can be accomplished to some extent by the specific configuration of the ribs 50. This can be further aided by any suitable machining operation following the formation of the aplicator tube. In the modified form of FIG. 11, slight enlargements or beads 92 may be formed at the tip ends of the segments 19. Preferably, the beads or enlargements 92 would be formed as a separate step following completion of the applicator tube; otherwise, to form the beads as part of the ejection molding process would tend to result in some irregularity in the formation of the segments owing to the uneven or increased wall thickness at the tips and uneven curing of the material. For instance, the beads or protective edges 92 may be formed by bonding a droplet of plastic to each of the tips 20 of the applicator tube after the injection-molding operation.

It is therefore to be understood that while a preferred and modified forms of hygienic applicator assembly and method of making same have been described, together with possible alternatives to the construction and design of the applicator assembly, various other modifications, variations and equivalent arrangements for such assembly and method may be resorted to which fall within the scope of the present invention as defined by the appended claims and reasonable equivalents thereof.

I claim:

1. A hygienic applicator assembly comprising:
  a thin-walled shell of generally tubular configuration having an outer wall along its greater length adapted to contain a hygienic medium therein and a generally dome-shaped end at one end of said shell defined by a series of resilient fingers converging forwardly in a radial direction from the one end of said outer wall, each of said fingers having inclined side edges converging forwardly toward one another in a generally circumferential direction to terminate in a common, rounded terminal end, and a clearance space formed between the inclined side edges of adjacent said fingers; and
  male inserter means of a length corresponding substantially to that of said thin-walled shell, said male inserter means being movable in close-fitting telescoping relation through the one end of said thin-walled shell, said male inserter means having a convergent sidewall adjacent to its leading end conforming substantially to the contour and length of said resilient fingers, said convergent sidewall terminating in a closed, forwardly convergent leading end conforming substantially to the contour of said rounded terminal end of said resilient fingers.

2. A hygienic applicator assembly according to claim 1, said fingers each being self-supporting and composed of a resilient material whereupon ejection of a hygienic medium contained in said thin-walled shell by said male inserter means, said fingers are operative to expand in an outward radial direction under the opening pressure of the hygienic medium and to contract against said convergent sidewall upon discharge of the hygienic medium therefrom.

3. A hygienic applicator assembly according to claim 2, there being a series of four triangular fingers arranged uniformly in circumferentially spaced relation about the one end of said outer shell, the bases of said triangular fingers being located at the one end of said outer wall of said thin-walled shell.

4. A hygienic applicator assembly according to either of claims 1 or 3, said shell having a plurality of inwardly directed projections disposed in circumferentially spaced relation about the inner surface of said outer wall adjacent to the rearward open end of said outer wall, said outer wall tapering forwardly toward said resilient fingers with the diameter of said outer wall at said one end corresponding to the effective diameter of said outer wall between said projections.

5. A hygienic applicator assembly according to claim 1, the rearward open end of said outer wall and the rearward end of said male inserter means each having a radially outwardly directed, unitary gripping ring extending therefrom.

6. A hygienic applicator assembly according to claim 4, each of said triangular fingers having a base in the form of a quadrant of a circle whose diameter corresponds to that at said one end of said outer thin-walled shell, the base of each triangular finger being greater than the height of each said triangular finger.

7. A hygienic applicator assembly according to claim 6, each of said traingular fingers provided with a bead at its forward, common terminal end.

8. A hygienic applicator assembly comprising in combination:

an outer, generally thin-walled shell of tubular configuration having a forwardly tapering outer wall along its greater length adapted to contain a hygienic medium therein and provided with a gripping ring at one end and an opposite segmental end being defined by a series of segments converging forwardly from said outer wall in an inward radial direction, each of said segments being of generally triangular configuration having inclined, equilateral side edges converging forwardly toward one another to terminate in a common, rounded terminal end with a forwardly divergent, open slotted area being formed between said side edges of adjacent of said triangular segments; and a plunger of a length corresponding substantially to that of said outer wall of said shell and a maximum diameter corresponding to the diameter of said outer wall at its juncture with said segmented end, said plunger movable in telescoping relation through said open end of said outer wall and having a forwardly convergent leading end conforming substantially to the contour of said segmented end of said outer shell.

9. A hygienic applicator assembly according to claim 8, including locator means in the form of radially inwardly directed dimples on the inner surface of said outer wall adjacent to the rearward end of said outer wall whereby to guide said plunger in close-fitting relation through the rearward open end of said outer wall, and limit means on said plunger to limit the forward projection of said plunger through said shell.

10. A hygienic applicator assembly according to claim 9, said plunger being of uniform diameter throughout its length which diameter corresponds to that of said locator means, and said outer wall being tapered in a forward direction from said locator means to a diameter corresponding to that of said plunger at the forward end of said outer wall.

11. A hygienic applicator assembly according to claim 8, said plunger being of generally tubular configuration having a rearward open end and a radially outwardly extending flange at said rearward open end provided with forwardly directed projections defining said limit means.

12. A hygienic applicator assembly according to claim 11, said forwardly convergent leading end of said plunger being of generally frusto-conical configuration and terminating in a squared end surface.

13. In a hygienic applicator, an exterior, thin-walled shell having an outer wall extending its greater length adapted to receive a hygienic medium therein said shell being provided with a rearward open end at one end of said outer wall and a plurality of corresponding, generally triangular segments converging forwardly in a generally radial direction from the opposite end of said wall, said triangular segments composed of a resilient material and having inclined side edges converging forwardly toward one another in a generally circumferential direction to terminate in a rounded terminal end forming the apex of each triangular segment, each of said triangular segments provided with a bead at its forward, common terminal end.

14. In a hygienic applicator according to claim 13, said outer wall of said shell tapering gradually in a forward direction throughout its greater length, and said triangular segments converging forwardly at an acute angle to the leading tapered end of said outer wall.

15. In a hygienic applicator according to claim 14, each said triangular segment in its relaxed state being disposed in closely-spaced relation to each adjacent segment, each segment having an inclined, straight wall section converging forwardly from said outer wall and terminating in a radially inwardly curved extremity at its rounded terminal end.

16. In a hygienic applicator according to claim 13, said segments each being self-supporting and composed of a resilient material, there being a series of four triangular segments arranged uniformly in circumferentially spaced relation about the one end of said outer wall, the bases of said triangular segments being located at the forward end of said outer wall of said thin-walled shell.

17. In a hygienic applicator according to claim 16, wherein a plurality of inwardly directed projections are formed in circumferentially spaced relation about the inner surface of said outer wall adjacent to the rearward open end of said outer wall, the rearward open end of said outer wall having a radially outwardly directed, unitary finger gripping ring extending therefrom.

18. In a hygienic applicator according to claim 13, each of said segments having a base in the form of a quadrant of a circle whose diameter corresponds to that of said outer thin-walled shell, the base of each segment being greater than the height of each said triangular segment.

19. A suppository applicator comprising in combination:

an outer, generally thin-walled shell of tubular configuration having a forwardly tapering outer wall adapted to contain a generally bullet-shaped suppository therein, said shell having a split end defined by a series of resilient triangular segments converging forwardly from said outer wall in an inward radial direction and curving radially inwardly at their forward extremities, each of said segments having inclined, equilateral side edges converging forwardly toward one another to terminate in a common, rounded terminal end at each said forward extremity with a forwardly divergent, open slotted area being formed between side edges of adjacent of said triangular segments; and a tubular plunger of a length corresponding substantially to that of said shell, said plunger movable in telescoping relation through said open end of said outer wall and having a forwardly convergent sidewall conforming substantially to the contour and length of said split end of said outer shell, said plunger having limit stop means to limit the forward projection of said leading end to a point adjacent to said forward extremities of said triangular segments.

20. A suppository applicator according to claim 19, including locator means in the form of radially inwardly directed portions on the inner surface of said outer wall adjacent to the rearward end of said outer wall whereby to guide said plunger in close-fitting relation through the rearward open end of said outer wall.

21. A suppository applicator according to claim 20, said plunger being of uniform diameter throughout its length, and said outer wall of said shell being tapered in a forward direction from a diameter slightly greater than that of said plunger to a diameter corresponding to that of said plunger at the forward end of said outer wall.

22. A suppository applicator according to claim 19, said plunger being of generally tubular configuration having a rearward open end, and said convergent sidewall being of generally frusto-conical configuration having an inclined straight wall section terminating in a more sharply convergent leading end.

* * * * *